US010774391B2

(12) United States Patent
Kana et al.

(10) Patent No.: US 10,774,391 B2
(45) Date of Patent: Sep. 15, 2020

(54) **GENETICALLY MODIFIED STRAINS OF *MYCOBACTERIUM SMEGMATIS***

(71) Applicant: UNIVERSITY OF THE WITWATERSRAND, JOHANNESBURG, Johannesburg (ZA)

(72) Inventors: Bavesh Davandara Kana, Johannesburg (ZA); Edith Erika Machowski, Johannesburg (ZA)

(73) Assignee: UNIVERSITY OF THE WITWATERSRAND, JOHANNESBURG, Johannesburg (ZA)

(*) Notice: Subject to any disclaimer, the term of this patent is extended or adjusted under 35 U.S.C. 154(b) by 0 days.

(21) Appl. No.: 16/090,530

(22) PCT Filed: Mar. 31, 2017

(86) PCT No.: PCT/IB2017/051857
§ 371 (c)(1),
(2) Date: Oct. 1, 2018

(87) PCT Pub. No.: WO2017/168384
PCT Pub. Date: Oct. 5, 2017

(65) Prior Publication Data

US 2019/0112639 A1 Apr. 18, 2019

(30) Foreign Application Priority Data

Mar. 31, 2016 (ZA) ................................ 2016/02181

(51) Int. Cl.
*C12Q 1/689* (2018.01)
*C07K 14/195* (2006.01)
*C07K 14/31* (2006.01)
*C07K 14/35* (2006.01)
*C12N 15/74* (2006.01)

(52) U.S. Cl.
CPC ............ *C12Q 1/689* (2013.01); *C07K 14/195* (2013.01); *C07K 14/31* (2013.01); *C07K 14/35* (2013.01); *C12N 15/74* (2013.01); *C12Q 2600/166* (2013.01)

(58) Field of Classification Search
None
See application file for complete search history.

(56) References Cited

U.S. PATENT DOCUMENTS 5,583,038 A * 12/1996 Stover .................... C07K 14/20
435/252.3

FOREIGN PATENT DOCUMENTS

WO 2012/078773 6/2012

OTHER PUBLICATIONS

Parisi et al. Anal Bioanal Chem (2008) 391:2127-2134.*
Definition of kit. Oxford Dictonaries Online. http://oxforddictionaries.com/search?q=kit&view=uk retrieved Aug. 13, 2010.*
Zainuddin et al. Molecular Microbiology (1989) 3(1), 29-34.*
Ito et al. Antimicrobial Agents and Chemotherapy, Jun. 1999, vol. 43, No. 6 p. 1449-1458.*
International Search Report and Written Opinion for Int. App. No. PCT/IB2017/051857, dated May 31, 2017.
Blakemore, R., et al., "Evaluation of the Analytical Performance of the Xpert MTB/RIF Assay," Journal of Clinical Microbiology, 2010, vol. 48, No. 7, p. 2495-2501.
Kolk, A. H. J., et al., "Mycobacterium smegmatis strain for detection of *Mycobacterium tuberculosis* by PCR used as internal control for inhibition of amplification and for quantification of bacteria," Journal of Clinical Microbiology, 1994, vol. 32, Nr:5, pp. 1354-1356.
Kox, L. F. F., et al., "Microwell hybridization assay for detection of PCR products from *Mycobacterium tuberculosis* complex and the recombinant *Mycobacterium smegmatis* strain 1008 used as an internal control," Journal of Clinical Microbiology, 1996, vol. 34, No. 9, p. 2117-2120.
Wolk, D. M., et al., "Rapid Detection of *Staphylococcus aureus* and Methicillin-Resistant *S. aureus* (MRSA) in Wound Specimens and Blood Cultures: Multicenter Preclinical Evaluation of the Cepheid Xpert MRSA/SA Skin and Soft Tissue and Blood Culture Assays," Journal of Clinical Microbiology, 2009, vol. 47, Nr:3, pp. 823-826.

* cited by examiner

*Primary Examiner* — Oluwatosin A Ogunbiyi
(74) *Attorney, Agent, or Firm* — McDonnell Boehnen Hulbert & Berghoff LLP

(57) ABSTRACT

The present invention relates to a recombinant bacterium based on a non-pathogenic bacterium that has a modified genome containing a nucleic acid of interest from a pathogen that is detected by a molecular diagnostic assay and that mimics the diagnostic profile of the pathogen. The invention further relates to a diagnostic control composition comprising the recombinant bacterium and to methods for producing the recombinant bacterium. The recombinant bacterium is a safe, reliable quality control for the detection of pathogens such as *Mycobacterium tuberculosis* and *Staphylococcus aureus*. The invention also relates to a kit comprising either the recombinant bacterium, compositions containing the recombinant bacterium or bacteria produced according to the method of the invention.

8 Claims, 3 Drawing Sheets

Specification includes a Sequence Listing.

| | TUB | WT1 | WT2 | WT3 | WT4 | WT5 | WT6 | WT7 | WT8 | MUT1 | MUT2A | MUT2B | MUT3 |
|---|---|---|---|---|---|---|---|---|---|---|---|---|---|
| mc²155 | | ▇ | ▭ | ▭ | ▇ | ▇ | ▭ | ▭ | ▭ | ▭ | ▭ | ▭ | ▭ |
| dreem1 RRDR$_{SM}$ | ▭ | ▇ | ▇ | ▇ | ▇ | ▇ | ▇ | ▇ | ▇ | ▭ | ▭ | ▭ | ▭ |
| dreem2 RRDR$_{TB}$ | ▭

GENETICALLY MODIFIED STRAINS OF *MYCOBACTERIUM SMEGMATIS*

CROSS REFERENCE TO RELATED APPLICATIONS

The present application is a U.S. National Phase Application pursuant to 35 U.S.C. of International Application No. PCT/IB2017/051857 filed Mar. 31, 2017, which claims priority to South African Patent Application No. 2016/02181 filed Mar. 31, 2016. The entirety of the disclosure of each of these applications is hereby incorporated by reference into the present application.

BACKGROUND OF THE INVENTION

The present invention relates to a recombinant bacterium based on a non-pathogenic bacterium that has a modified genome containing a nucleic acid of interest from a pathogen that is detected by a molecular diagnostic assay and that mimics the diagnostic profile of the pathogen. The invention further relates to a diagnostic control composition comprising the recombinant bacterium and to methods for producing the recombinant bacterium. The recombinant bacterium is a safe, reliable quality control for the detection of pathogens such as *Mycobacterium tuberculosis* and *Staphylococcus aureus*.

Tuberculosis (TB) is a devastating disease that is recalcitrant to effective clinical management. Its robust nature combined with outdated diagnostic methods have made treatment at the point of care increasingly difficult, especially in the ever-increasing prevalence of drug resistant strains. With diagnostics in many microbial diseases shifting away from bacteriologic culture and microscopic identification methods towards molecular biological systems, automation requires stringent calibration to ensure sensitivity and specificity of the results. The World Health Organisation (WHO) has endorsed two nucleotide amplification assay (NAA) diagnostic tests for standard identification of *Mycobacterium tuberculosis* in pulmonary patients that can simultaneously identify the organism as well as assess RIF and/or INH resistance, namely GeneXpert MTB/RIF (Cepheid Innovation) and the GenoType MDRTBplus Line Probe Assay (LPA) (Hain Lifescience®). This has empowered clinicians in tailoring drug regimens for patients, thereby not only improving treatment outcomes but also restricting spread in communities. Here we report modified strains of the related non-pathogenic soil bacterium *Mycobacterium smegmatis* that mimic the diagnostic profile of $H_{37}Rv$ in both the GeneXpert® MTB/RIF (Xpert® MTB/RIF) and the Hain-Lifescience® LPA, in terms of both organism identification and RIF resistance profiling. To extend this approach to other diseases we also show that a *Staphylococcus aureus* gene sequence can be introduced into *Mycobacterium smegmatis* to generate a positive response in the GeneXpert® SA Nasal complete (Xpert®-SANC) cartridge, designed for identification of methicillin resistance in *Staphylococcus aureus*. This finding demonstrates that this application holds promise across diagnostic platforms for production of a surrogate positive NAA signal from a non-infectious organism. Currently the calibration standards for the Xpert® MTBIRIF assay are produced in a laboratory strain of *Mycobacterium tuberculosis* $H_{37}Rv$, the procedure of which is lengthy, hazardous and costly as it requires mass production of live bacteria which are then killed to make them safe to handle and transport. The modified *Mycobacterium smegmatis* holds promise as a replacement for large scale calibration standard production, external quality assessment and general clinical surveillance as worldwide demand of these diagnostics is expected to increase.

The current regimen for TB treatment prescribed by the WHO consists of four drugs: isoniazid (INH), pyrazinamide (PZA), ethambutol (EMB) and rifampicin (RIF)). RIF is potent at killing *Mycobacterium tuberculosis* through binding of the RNA polymerase (RNAP) beta subunit RpoB of the transcription complex, thus inhibiting the synthesis of RNA and consequently proteins. Resistance develops by non-synonymous amino acid substitutions that prevent the binding of RIF to the active site of RNAP, whilst retaining functionality of the complex. In the presence of RIF, in the clinic and the laboratory, sensitive strains are selected against, leading to an outgrowth of drug resistant mutant strains. Whilst mutation to RIF resistance ($RIF^R$) carries a fitness cost under normal growth conditions, these resistant strains have ensured their own survival by their chromosomally encoded adaptation under conditions in which all other RIF susceptible ($RIF^S$) strains die.

The majority of $RIF^R$ strains have single nucleotide polymorphism (SNP) mutations confined to a limited sequence within the rpoB gene, the 81 bp RIF resistance determining region (RRDR). As one of the first line anti-tubercular drugs, the efficacy and low cost of RIF is critical for continued use against drug sensitive clinical strains. Prevention of morbidity and mortality is compromised by the treatment of patients infected with resistant strains which are non-responsive to antibiotics in the regimen. In addition, these patients contribute to spread of resistant bacteria in communities. In order for clinicians to make informed decisions, smear microscopy is no longer sufficient. Ideally drug susceptibility testing (DST) needs to be performed alongside identification of the causative agent *Mycobacterium tuberculosis*.

Strains that are multidrug resistant (MDR), i.e. no longer responsive to RIF and INH, are effectively treated with only EMB and PZA, and in the process are more likely to evolve further resistance to these drugs. It is then necessary to switch to alternate drug regimens to ensure continued efficacy. Drug therapy to combat MDR-TB is significantly more expensive, requiring at least 5 different drugs from an array consisting of fluoroquinolones (levofloxacin or moxifloxacin), injectable drugs (amikacin, kanamycin or capreomycin), oral bacteriostatic drugs (prothionamide, ethionamide, cycloserine or para-aminosalicylic acid) and pyrazinamide for up to 2 years. Patient compliance is a major risk factor, especially for the injectable drugs which require clinical administration.

Due to the slow growth of *Mycobacterium tuberculosis* in vitro, lengthy culture times are required to obtain growth of bacteria for identification, followed by additional culture in the presence or absence of antibiotic to test for resistance. The current gold standard for growth assessment by liquid culture is the BACTEC™ MGIT™ (mycobacterial growth indicator tubes) in which a test is considered negative only after 42 days. If at any time before that bacteria emerge, this test is considered positive. As a result, it can again take 42 days to make a decision regarding infection and a further 42 days more to determine the drug resistance of the organism. This can lead to patients being treated with ineffective antibiotics in the interim, during which time their health will deteriorate and the strain will potentially spread.

Recent developments in molecular diagnostic methods have significantly improved upon culture methods, as they probe the sputum sample directly for the presence of the bacterial chromosome. It is for this reason that in 2010 the WHO endorsed two nucleic acid amplification (NAA) diagnostic assays for TB. The GeneXpert® real time PCR platform has been developed for use with a number of different assays. The Xpert® MTB/RIF assay utilises molecular beacon technology that allows for real time signal produced by NAA. As the amount of nucleic acid increases with every round of amplification, more fluorescent signal is released and highly specific sequence can be detected. The test is entirely automated and requires little instruction or skill of clinical staff, wither for operation or evaluation of results.

The Xpert®-MTB/RIF system relies on a fixed set of gene probes that can specifically identify the *Mycobacterium tuberculosis*-specific sequence and differentiate it from other bacteria that differ marginally, including non-tuberculous mycobacteria and related soil bacteria. These differences, although discernible at the molecular level, are non-synonymous and do not affect the peptide sequence of the gene nor the function of the resulting RpoB protein. The same principle allows GeneXpert® to identify *Mycobacterium tuberculosis*-specific sequence which does not match the wild type sequence at different positions. In this case however the peptide sequence is altered leading to mutant proteins. This is the cause of the phenotype that results in antibiotic resistance.

The principle behind the molecular line probe assay (LPA) (Genotype® MTBDR plus assay, HAIN Lifescience®, Germany) differs in that it generates information about the presence or absence of nucleic acid content related to drug resistance at the endpoint of the amplification procedure. Several steps of processing are involved and each requires a number of parallel controls, and the procedure requires technically skilled personnel.

*Staphylococcus aureus* is a gram-positive, round-shaped bacterium frequently found in the nose, respiratory tract, and on the skin. Although *Staphylococcus aureus* is not always pathogenic, it is a common cause of skin infections such as a skin abscess, respiratory infections such as sinusitis, and food poisoning. Pathogenic strains often promote infections by producing virulence factors such as potent protein toxins, and the expression of cell-surface proteins that bind and inactivate antibodies.

The emergence of antibiotic-resistant strains of *Staphylococcus aureus* such as methicillin-resistant *Staphylococcus aureus* (MRSA) is a worldwide problem in clinical medicine. MRSA is believed to have evolved by acquiring a mobile genetic element, the Staphylococcal cassette chromosome (SCC) by horizontal transfer from another species. The SCCmec cassette carries the mecA gene which confers methicillin resistance. Despite much research and development there is no approved vaccine for *Staphylococcus aureus*. Over 278,000 hospitalized persons are infected by MRSA annually and MRSA accounts for over 60% of hospital-acquired *Staphylococcus aureus* infections in the United States. MRSA strains are particularly virulent, spread rapidly and cause more severe infections than other Staphylococcal bacteria. Early detection of MRSA and the ability to distinguish MRSA from methicillin-sensitive *Staphylococcus aureus* assists in limiting the spread of infection, determining treatment options and reducing healthcare burden. It has been shown that active surveillance of MRSA infections optimises effectiveness and control programs from MRSA outbreaks.

The GeneXpert® MRSA assay (Xpert®-MRSA) targets DNA sequences in the region of the open reading frame orfX where the staphylococcal cassette chromosome mec (SCCmec) integrates into the *Staphylococcus aureus* chromosome. SCCmec carries the resistance determinant mecA, which encodes methicillin resistance and exhibits at least six different structural types and numerous subtypes.

The Xpert®-MRSA and Xpert®-SANC are widely used in active surveillance of MRSA. However, there is presently no calibration or surveillance standard for testing the accuracy of the test as applied to surveillance testing in order to reduce false positive and negative results.

The use of live strains of bacteria as positive controls in diagnostic testing is undesirable for virulent bacteria as they pose a risk for the operator in ordinary handling in the laboratory. Killing these bacteria to produce a positive control requires the use of specialised laboratories with skilled staff.

In this work we have generated strains of the soil bacterium *Mycobacterium smegmatis*, a non-pathogenic relative of *Mycobacterium tuberculosis*, to test whether it is possible to utilise these as verification standards for diagnostic procedures. GeneXpert® assays and the Hain Lifescience® LPA require controls that confirm the accuracy of the assays. The *Mycobacterium smegmatis* strains reported herein contain nucleotide sequences introduced from either *Mycobacterium tuberculosis* or *Staphylococcus aureus* that mimic the diagnostic profile of clinical strains. These strains are expected to significantly reduce the cost, time and biohazard risk in the production of verification standards, with possible applicability across other NAA platforms.

SUMMARY OF THE INVENTION

The present invention relates to a recombinant bacterium having a modified genome including a nucleic acid of interest which is detectable by a molecular diagnostic assay such that the recombinant bacterium mimics the diagnostic profile of a pathogen of interest in the assay.

According to a first aspect of the present invention there is provided for a recombinant bacterium, wherein the recombinant bacterium is a non-pathogenic bacterium having a modified genome containing a nucleic acid of interest from a pathogen, wherein the nucleic acid of interest is detectable by a molecular diagnostic assay and wherein the recombinant bacterium mimics the diagnostic profile of the pathogen.

In a preferred embodiment of the invention the non-pathogenic bacterium is *Mycobacterium smegmatis*.

In a second embodiment of the invention, the pathogen may be selected from the group consisting of *Acinetobacter* spp., *Actinobacillus* spp., *Actinomycetes* spp., *Aeromonas* spp., *Bacillus* spp., *Bordetella* spp., *Borrelia* spp., *Brucella* spp., *Campylobacter* spp., *Chlamydia* spp., *Clostridium* spp., *Corynebacterium* spp., *Enterobacter* spp., *Enterococcus* spp., *Erwinia* spp., *Erysipelothrix* spp., *Escherichia* spp., *Francisella* spp., *Klebsiella* spp., *Haemophilus* spp., *Legionella* spp., *Leptospira* spp., *Listeria* spp., *Moraxella* spp., *Mycobacterium* spp., *Mycoplasma* spp., *Neisseria* spp., *Nocardia* spp., *Pasteurella* spp., *Pseudomonas* spp., *Rickettsia* spp., *Salmonella* spp., *Shigella* spp., *Spirillum* spp., *Staphylococcus* spp., *Streptobacillus* spp., *Streptococcus* spp., *Streptomyces* spp., *Treponema* spp., *Vibrio* spp., *Yersinia* spp. and *Xanthomonas* spp. Preferably the pathogen is *Mycobacterium tuberculosis* or *Staphylococcus aureus*.

According to a third embodiment of the invention the nucleic acid of interest may include a rifampicin resistance determining region (RRDR) from *Mycobacterium tuberculosis* such that the recombinant bacterium mimics the diagnostic profile of a rifampicin resistant *Mycobacterium tuberculosis* strain in the molecular diagnostic assay. The nucleic acid of interest including the RRDR region from *Mycobac-*

*terium tuberculosis* may have a sequence selected from the group consisting of SEQ ID NOs:1-6 or SEQ ID NOs:9-14.

In an alternative embodiment of the invention the nucleic acid of interest includes a SCCmec junction region of *Staphylococcus aureus* such that the recombinant bacterium mimics the diagnostic profile of a methicillin resistant *Staphylococcus aureus* strain in the molecular diagnostic assay. The nucleic acid of interest including the SCCmec junction may have the sequence of SEQ ID NO:8.

In a further embodiment of the invention the recombinant bacterium further includes a selection marker to facilitate growth of the strain in laboratory media.

In yet another embodiment of the invention the nucleic acid of interest is contained on a vector and the recombinant bacterium is transformed with the vector. It will be appreciated the recombinant bacterium is either stably or transiently transformed with the vector including the nucleic acid of interest.

According to a second aspect of the invention there is provided for a diagnostic control composition comprising the recombinant bacterium of the invention, particularly wherein the diagnostic control composition is a positive control for a molecular diagnostic assay.

According to a third aspect of the present invention there is provided for a method of producing a recombinant bacterium that mimics the diagnostic profile of a pathogen in a molecular diagnostic assay, the method comprising:

(i) transforming a non-pathogenic bacterium with a vector, wherein the vector comprises a nucleic acid of interest from the pathogen and a selection marker, preferably an antibiotic selection marker, and further wherein the nucleic acid of interest is capable of being detected by the molecular diagnostic assay; and (ii) culturing the recombinant bacterium obtained in step (i) under selective conditions in order to select the recombinant bacterium.

In a preferred embodiment of the invention the non-pathogenic bacterium is *Mycobacterium smegmatis*.

According to a further embodiment the pathogen is selected from the group consisting of *Acinetobacter* spp., *Actinobacillus* spp., *Actinomycetes* spp., *Aeromonas* spp., *Bacillus* spp., *Bordetella* spp., *Borrelia* spp., *Brucella* spp., *Campylobacter* spp., *Chlamydia* spp., *Clostridium* spp., *Corynebacterium* spp., *Enterobacter* spp., *Enterococcus* spp., *Erwinia* spp., *Erysipelothrix* spp., *Escherichia* spp., *Francisella* spp., *Klebsiella* spp., *Haemophilus* spp., *Legionella* spp., *Leptospira* spp., *Listeria* spp., *Moraxella* spp., *Mycobacterium* spp., *Mycoplasma* spp., *Neisseria* spp., *Nocardia* spp., *Pasteurella* spp., *Pseudomonas* spp., *Rickettsia* spp., *Salmonella* spp., *Shigella* spp., *Spirillum* spp., *Staphylococcus* spp., *Streptobacillus* spp., *Streptococcus* spp., *Streptomyces* spp., *Treponema* spp., *Vibrio* spp., *Yersinia* spp. and *Xanthomonas* spp. Preferably the pathogen is *Mycobacterium tuberculosis* or *Staphylococcus aureus*.

In yet another embodiment of the invention the nucleic acid of interest may include a rifampicin resistance determining region (RRDR) from *Mycobacterium tuberculosis* such that the recombinant bacterium mimics the diagnostic profile of a rifampicin resistant *Mycobacterium tuberculosis* strain in the molecular diagnostic assay. The nucleic acid of interest including the RRDR region from *Mycobacterium tuberculosis* may have a sequence selected from the group consisting of SEQ ID NOs:1-6 or SEQ ID NOs:9-14.

In an alternative embodiment of the invention the nucleic acid of interest includes a SCCmec junction region of *Staphylococcus aureus* and the recombinant bacterium mimics the diagnostic profile of a methicillin resistant *Staphylococcus aureus* strain in the molecular diagnostic assay. The nucleic acid of interest including the SCCmec junction may have the sequence of SEQ ID NO:8.

In yet a further embodiment of the invention the nucleic acid of interest is contained on a vector and the recombinant bacterium is transformed with the vector. It will be appreciated the recombinant bacterium is either stably or transiently transformed with the vector including the nucleic acid of interest.

According to a fourth aspect of the present invention there is provided for a kit comprising the recombinant bacterium or the diagnostic control composition of the invention and instructions for use.

BRIEF DESCRIPTION OF THE FIGURES

Non-limiting embodiments of the invention will now be described by way of example only and with reference to the following figures.

SEQUENCE LISTING

Figure 1:
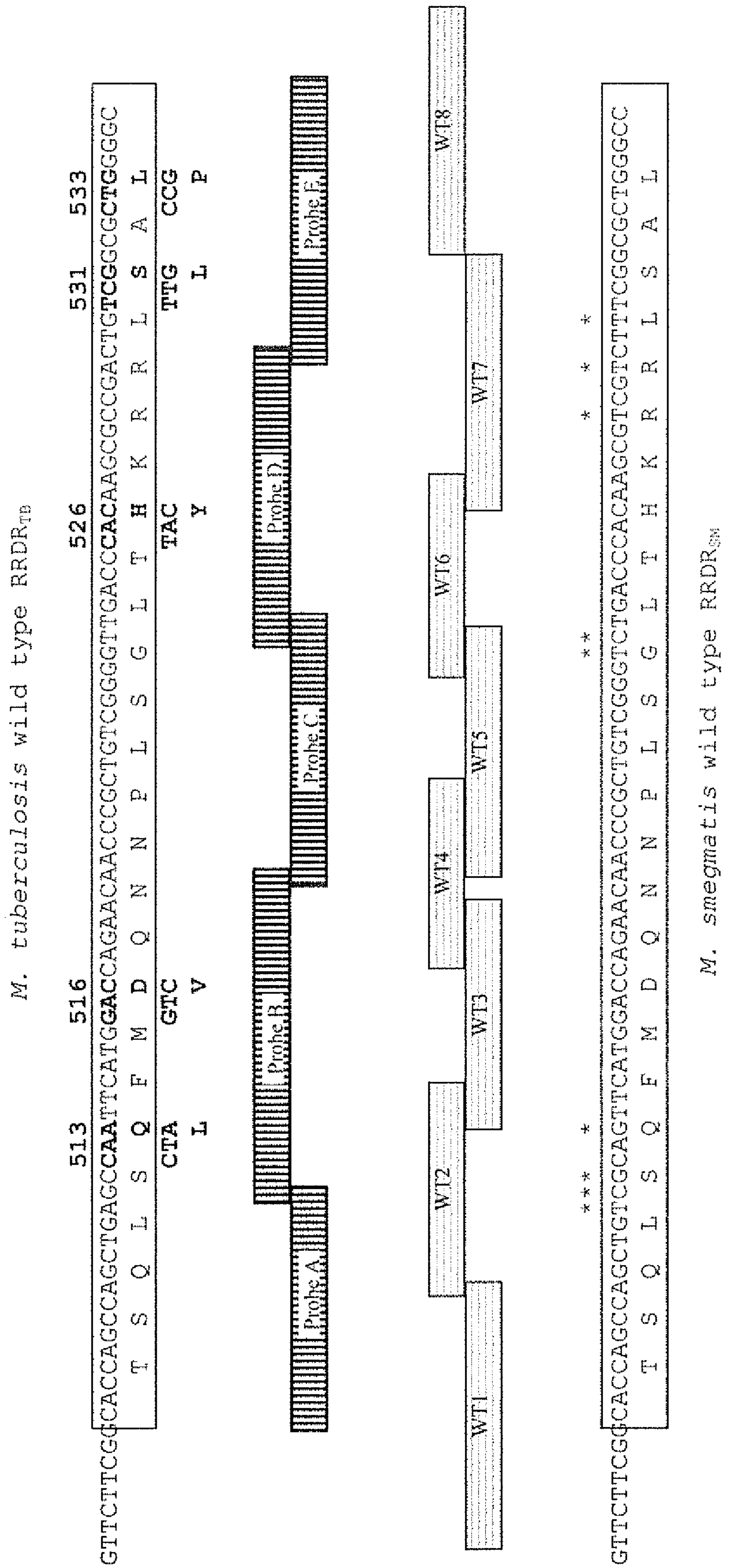
FIG. 1: RIF Resistance Determining Regions RRDR of *Mycobacterium tuberculosis* and *Mycobacterium smegmatis*. Nucleotide changes within RRDR can result in altered RpoB peptide sequence. Grey boxes denote the location of amino acid changes of $RIF^R$ strains in dreem2 to dreem6 within $RRDR_{TB}$, that allow for Xpert® MTBIRIF to classify bacteria as $RIF^R$. The SNPs at positions 513, 516, 526, 531, and 533 are also shown. Because of non-homology the respective probes do not bind and no fluorescence is obtained in those channels. Asterisks indicate the location of the nucleotide differences between $RRDR_{TB}$ and $RRDR_{SM}$. There are no amino acid differences between the wild type *Mycobacterium tuberculosis* and *Mycobacterium smegmatis* RpoB in this region.
Figure 2:
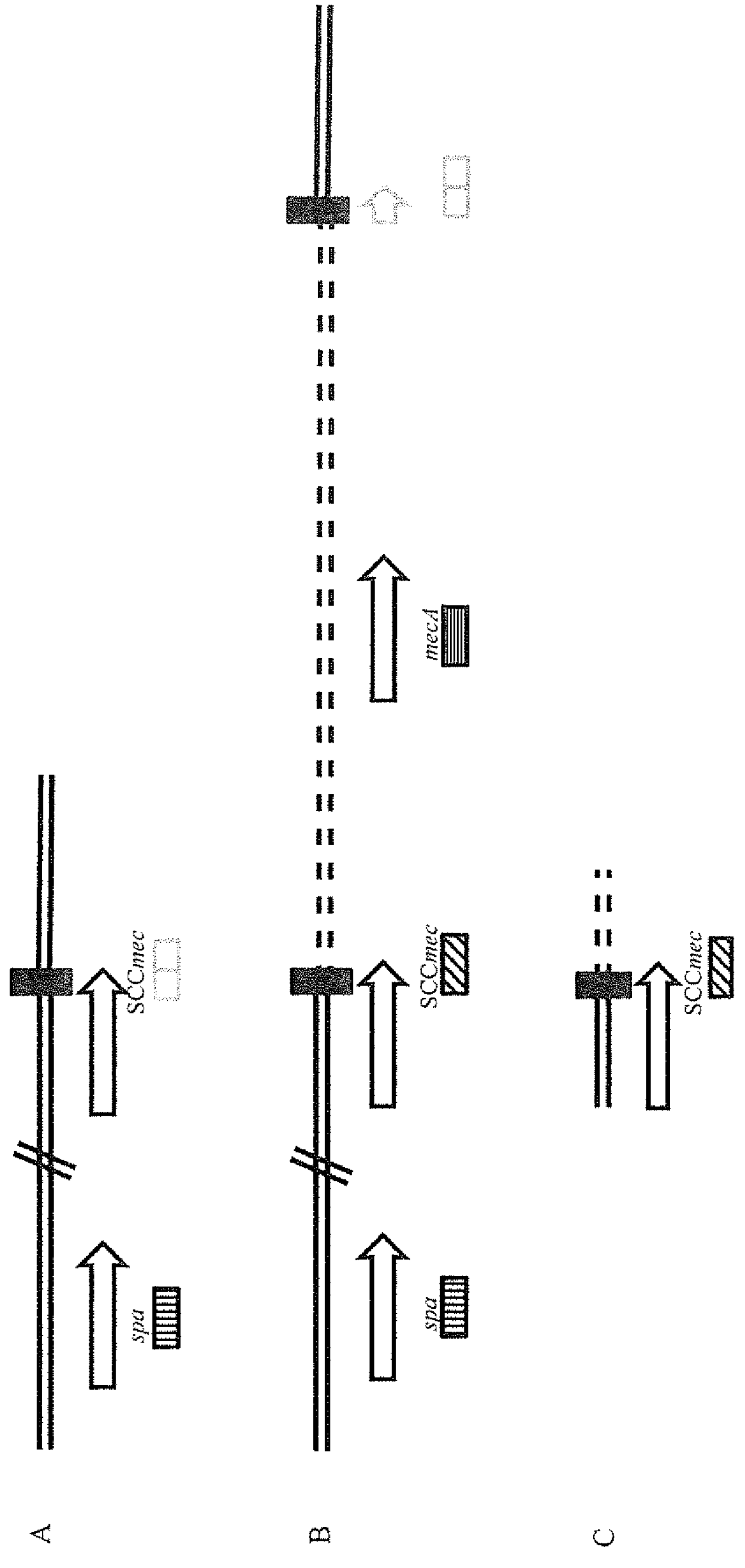
FIG. 2: *Staphylococcus aureus* genomic elements utilised for the Xpert®-SANC diagnostic assay (not to scale). Boxes below genes indicate the location of probe hybridising regions. Shaded boxes: positive for fluorescent signal. Empty boxes: Lack of fluorescent signal. spa denotes the *Staphylococcus aureus* specific gene used for speciation at a distal site in the chromosome (vertical bars). No signal is obtained if the orfX primers are juxtaposed with primers of wild type genomic region (grey boxes). Probe SCCmec specifically targets the attL junction at orfX and the mobile element (diagonal bars). mecA is the integrase gene that directs the mobile DNA elements to the attB site at the orfX locus (horizontal bars). Panel A: Chromosomal configuration of a wild type *Staphylococcus aureus* strain. Fluorescent signal is only obtained from the speciation probe spa. Panel B: Chromosomal configuration of a methicillin resistant strain. Signal using Xpert®-SANC is obtained from all three probes spa, mecA and SCCmec. The latter two are specific for MRSA strains. Diagonal slashes indicate that the spa gene is distal to the attB site. Panel C: Chromosomal configuration of the *Mycobacterium smegmatis* integration mutant dreemX. None of the probes bind to mycobacterial sequence. The artificially introduced SCCmec element allows for signal to be detected by Xpert®-SANC. Diagonal slashes indicate that the spa gene is distal to the attB site.

The nucleic acid and amino acid sequences listed in the accompanying sequence listing are shown using standard letter abbreviations for nucleotide bases, and the standard three letter abbreviations for amino acids. It will be understood by those of skill in the art that only one strand of each nucleic acid sequence is shown, but that the complementary strand is included by any reference to the displayed strand. In the accompanying sequence listing:

SEQ ID NO:1—Nucleotide sequence of RRDR of *Mycobacterium tuberculosis* wild type strain H37Rv SEQ ID NO:2—Nucleotide sequence of RRDR of *Mycobacterium tuberculosis* strain with Q513L allele SEQ ID NO:3—Nucleotide sequence of RRDR of *Mycobacterium tuberculosis* strain with D516V allele SEQ ID NO:4—Nucleotide sequence of RRDR of *Mycobacterium tuberculosis* strain with H526Y allele SEQ ID NO:5—Nucleotide sequence of RRDR of *Mycobacterium tuberculosis* strain with S531L allele SEQ ID NO:6—Nucleotide sequence of RRDR of *Mycobacterium tuberculosis* strain with L533P allele SEQ ID NO:7—Nucleotide sequence of RRDR of *Mycobacterium smegmatis*

SEQ ID NO:8—Nucleotide sequence of *Staphylococcus aureus*-derived orfX and SCCmec region included in *Mycobacterium smegmatis* construct for MRSA assay SEQ ID NO:9—Nucleotide sequence of insert including RRDR of *Mycobacterium tuberculosis* wild type strain H37Rv used in construct SEQ ID NO:10—Nucleotide sequence of insert including RRDR of *Mycobacterium tuberculosis* strain with Q513L allele used in construct SEQ ID NO:11—Nucleotide sequence of insert including RRDR of *Mycobacterium tuberculosis* strain with D516V allele used in construct SEQ ID NO:12—Nucleotide sequence of insert including RRDR of *Mycobacterium tuberculosis* strain with H526Y allele used in construct SEQ ID NO:13—Nucleotide sequence of insert including RRDR of *Mycobacterium tuberculosis* strain with 8531L allele used in construct SEQ ID NO:14—Nucleotide sequence of insert including RRDR of *Mycobacterium tuberculosis* strain with L533P allele used in construct

DETAILED DESCRIPTION OF THE INVENTION

The present invention will now be described more fully hereinafter with reference to the accompanying drawings, in which some, but not all embodiments of the invention are shown.

The invention as described should not be limited to the specific embodiments disclosed and modifications and other embodiments are intended to be included within the scope of the invention. Although specific terms are employed herein, they are used in a generic and descriptive sense only and not for purposes of limitation.

As used throughout this specification and in the claims which follow, the singular forms “a”, “an” and “the” include the plural form, unless the context clearly indicates otherwise.

The terminology and phraseology used herein is for the purpose of description and should not be regarded as limiting. The use of the terms “comprising”, “containing”, “having” and “including” and variations thereof used herein, are meant to encompass the items listed thereafter and equivalents thereof as well as additional items.

The invention relates to a recombinant bacterium that mimics the diagnostic profile of a pathogen. The recombinant bacterium of the invention is based on a non-pathogenic bacterium that has a modified genome containing a nucleic acid of interest from a pathogen, wherein the nucleic acid of interest is detected by a molecular diagnostic assay.

The term “recombinant” means that something has been recombined. When used with reference to a nucleic acid construct, the term refers to a molecule that comprises nucleic acid sequences that are joined together or produced by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Accordingly, a recombinant nucleic acid construct indicates that the nucleic acid molecule has been manipulated using genetic engineering, i.e. by human intervention. Recombinant nucleic acid constructs may be introduced into a host cell by transformation and preferably by transformation with a vector.

The term “vector” refers to a means by which polynucleotides or gene sequences can be introduced into a cell. There are various types of vectors known in the art including plasmids, viruses, bacteriophages and cosmids. Generally polynucleotides or gene sequences are introduced into a vector by means of recombinant DNA technology.

The recombinant bacterium of the invention is preferably a recombinant *Mycobacterium smegmatis* bacterium. *Mycobacterium smegmatis* is preferred as this bacterium is non-pathogenic and does not require the same levels of biosafety for its propagation. It will be appreciated that the recombinant bacterium of the invention preferably has a modified genome containing a nucleic acid of interest which is detected by a diagnostic assay. However, due to the incorporation of the nucleic acid sequence of interest the recombinant *Mycobacterium smegmatis* mimics the diagnostic profile of the pathogen being detected, such as $RIF^R$ *Mycobacterium tuberculosis* or multi-drug resistant *Staphylococcus aureus*.

As used herein the terms “nucleic acid”, “nucleic acid molecule” or “polynucleotide” encompass both ribonucleotides (RNA) and deoxyribonucleotides (DNA), including cDNA, genomic DNA, and synthetic DNA. A nucleic acid may be double-stranded or single-stranded. Where the nucleic acid is single-stranded, the nucleic acid may be the sense strand or the antisense strand. A nucleic acid molecule may be any chain of two or more covalently bonded nucleotides, including naturally occurring or non-naturally occurring nucleotides, or nucleotide analogs or derivatives. The term “DNA” refers to a sequence of two or more covalently bonded, naturally occurring or modified deoxyribonucleotides.

The recombinant *Mycobacterium smegmatis* may be used as a control for the detection of a pathogen in a diagnostic assay. The pathogen may be a bacterium selected from the group consisting of *Acinetobacter* spp., *Actinobacillus* spp., *Actinomycetes* spp., *Aeromonas* spp., *Bacillus* spp., *Bordetella* spp., *Borrelia* spp., *Brucella* spp., *Campylobacter* spp., *Chlamydia* spp., *Clostridium* spp., *Corynebacterium* spp., *Enterobacter* spp., *Enterococcus* spp., *Erwinia* spp., *Erysip-*

*elothrix* spp., *Escherichia* spp., *Francisella* spp., *Klebsiella* spp., *Haemophilus* spp., *Legionella* spp., *Leptospira* spp., *Listeria* spp., *Moraxella* spp., *Mycobacterium* spp., *Mycoplasma* spp., *Neisseria* spp., *Nocardia* spp., *Pasteurella* spp., *Pseudomonas* spp., *Rickettsia* spp., *Salmonella* spp., *Shigella* spp., *Spirillum* spp., *Staphylococcus* spp., *Streptobacillus* spp., *Streptococcus* spp., *Streptomyces* spp., *Treponema* spp., *Vibrio* spp., *Yersinia* spp. and *Xanthomonas* spp. Preferably, the pathogen is selected from the group consisting of *Mycobacterium tuberculosis* and *Staphylococcus aureus*.

Particularly, the recombinant *Mycobacterium smegmatis* may be used as a control for a diagnostic assay for the detection of rifampicin resistant *Mycobacterium tuberculosis* or multi-drug resistant *Staphylococcus aureus*. More particularly, the recombinant *Mycobacterium smegmatis* may be used for the calibration of diagnostic devices used to diagnose the presence of rifampicin resistant *Mycobacterium tuberculosis* in a subject and active surveillance monitoring of MRSA infections. For example, the recombinant *Mycobacterium smegmatis* may be used as a control in the GeneXpert® system assays, such as Xpert® MTB/RIF assay, Xpert® SA Nasal Complete assay, Xpert® MRSA/SA SSTI assay, Xpert® MRSA/SA BC assay, Xpert® MRSA NXG assay, Xpert® Carba-R assay, Xpert® *C. difficile* assay, Xpert® *C. difficile*/Epi assay, Xpert® vanA assay, Xpert® CT/NG assay, Xpert® GBS assay, Xpert® GBS LB assay. The recombinant *Mycobacterium smegmatis* may also be used as a control in other diagnostic assays, such as the GenoType MDRTBplus Line Probe Assay, Anyplex™ II MTB/MDR Detection assay, Anyplex™ II MTB/XDR Detection assay, Anyplex™ II MTB/NTM Real-time Detection assay, Seeplex® MTB/NTM ACE Detection assay, Seeplex® MTB Nested ACE Detection assay, Magicplex™ Sepsis Real-time assay, Seeplex® Meningitis ACE Detection assay, Anyplex™ II RB5 Detection assay, Seeplex® PneumoBacter ACE Detection assay, Allplex™ STI/BV Panel Assay, Allplex™ STI Essential Assay, Allplex™ Bacterial Vaginosis Assay, Anyplex™ II STI-7 Detection assay, Anyplex™ II STI-5 Detection assay, or the Anyplex™ CTING Real-time Detection assay.

In one embodiment of the invention the recombinant *Mycobacterium smegmatis* is used for the purposes of external quality assessment (EQA) of the GeneXpert® modular cartridge system. In brief the GeneXpert® system relies on the use of complementary nucleic acid probes to detect the presence or absence of an RRDR nucleic acid in the MTB/RIF assay and the presence or absence of mecA in the MRSA assay, or substantially identical nucleic acids thereto, in a bacterium.

The term "complementary" refers to two nucleic acids molecules, e.g., DNA or RNA, which are capable of forming Watson-Crick base pairs to produce a region of double-strandedness between the two nucleic acid molecules. It will be appreciated by those of skill in the art that each nucleotide in a nucleic acid molecule need not form a matched Watson-Crick base pair with a nucleotide in an opposing complementary strand to form a duplex. One nucleic acid molecule is thus "complementary" to a second nucleic acid molecule if it hybridizes, under conditions of high stringency, with the second nucleic acid molecule. A nucleic acid molecule according to the invention includes both complementary molecules.

As used herein a "substantially identical" sequence is an amino acid or nucleotide sequence that differs from a reference sequence only by one or more conservative substitutions, or by one or more non-conservative substitutions, deletions, or insertions located at positions of the sequence that do not destroy or substantially reduce the antigenicity of one or more of the expressed polypeptides or of the polypeptides encoded by the nucleic acid molecules. Alignment for purposes of determining percent sequence identity can be achieved in various ways that are within the knowledge of those with skill in the art. These include using, for instance, computer software such as ALIGN, Megalign (DNASTAR), CLUSTALW or BLAST software. Those skilled in the art can readily determine appropriate parameters for measuring alignment, including any algorithms needed to achieve maximal alignment over the full length of the sequences being compared. In one embodiment of the invention there is provided for a polypeptide or polynucleotide sequence that has at least about 80% sequence identity, at least about 90% sequence identity, or even greater sequence identity, such as about 95%, about 96%, about 97%, about 98% or about 99% sequence identity to the sequences described herein.

Alternatively, or additionally, two nucleic acid sequences may be "substantially identical" if they hybridize under high stringency conditions. The "stringency" of a hybridisation reaction is readily determinable by one of ordinary skill in the art, and generally is an empirical calculation which depends upon probe length, washing temperature, and salt concentration. In general, longer probes required higher temperatures for proper annealing, while shorter probes require lower temperatures. Hybridisation generally depends on the ability of denatured DNA to re-anneal when complementary strands are present in an environment below their melting temperature. A typical example of such "stringent" hybridisation conditions would be hybridisation carried out for 18 hours at 65° C. with gentle shaking, a first wash for 12 min at 65° C. in Wash Buffer A (0.5% SDS; 2×SSC), and a second wash for 10 min at 65° C. in Wash Buffer B (0.1% SDS; 0.5% SSC).

Herein, the Applicant has generated strains of a non-pathogenic bacterial relative of *Mycobacterium tuberculosis, Mycobacterium smegmatis*, where the RRDR from *Mycobacterium tuberculosis* has been inserted into a plasmid that integrates into the attB phage attachment site. *Mycobacterium smegmatis* is not recognized by any of the GeneXpert® assays which detect *Mycobacterium tuberculosis* and the insertion of the RRDR from *Mycobacterium tuberculosis* into this organism allows it to be detected by the GeneXpert® assays which detect *Mycobacterium tuberculosis. The recombinant strains can carry a wild type, normal copy of the RRDR or a mutated version that is similar to that found in RIF*$^R$ patients. In addition, the Applicant has produced an *Mycobacterium smegmatis* strain carrying the sequence recognised by an SCCmec probe which specifically targets the attL junction at orfX and the mobile element of *Staphylococcus aureus. Mycobacterium smegmatis* is not recognized by any of the GeneXpert® assays which detect *Staphylococcus aureus* and the insertion of the attL junction at orfX and the mobile element allows it to be detected by the GeneXpert® assays which detect *Staphylococcus aureus*.

The following examples are offered by way of illustration and not by way of limitation.

Example 1

Bacterial Strains and Culture Conditions

All cloning was performed in *Escherichia coli* strain DH5a. Experiments were performed in *Mycobacterium smegmatis* strain mc$^2$155. All strains and plasmids used and generated are listed in Table 1 and Table 2, respectively. Nucleic acid sequence inserts used in the constructs are listed in Table 3.

TABLE 1

| Strains used and generated | | |
|---|---|---|
| Plasmid | Genotype | Source |
| *Escherichia.coli* DH5α | fhuA2 lac(del)U169 phoA glnV44 Φ80' lacZ(del)M15 gyrA96 recA1 relA1 endA1 thi-1 hsdR17 | Promega |
| *Mycobacterium smegmatis* $mc^2155$ | ept-1 | Snapper et al 1990 |
| dreem1 | $mc^2155$::RRDR-57-attP-int; hyg | This work |

TABLE 1-continued

| Strains used and generated | | |
|---|---|---|
| Plasmid | Genotype | Source |
| dreem2 | $mc^2155$::513-57-attP-int; hyg | This work |
| dreem3 | $mc^2155$::516-57-attP-int; hyg | This work |
| dreem4 | $mc^2155$::526-57-attP-int; hyg | This work |
| dreem5 | $mc^2155$::531-57-attP-int; hyg | This work |
| dreem6 | $mc^2155$::533-57-attP-int; hyg | This work |
| dreemX | $mc^2155$::orfX-SCC junction-attP-int; hyg | This work |

TABLE 2

| Plasmids used and generated | | |
|---|---|---|
| Plasmid | Genotype | Source |
| pHINT | oriE; bla; hyg; L5-attP-int | Stover at al |
| RRDR-XhoI-ClaI | H37Rv wild type RRDR in pUC57simple; bla | GenScript |
| RRDR_Q513L | RRDR-XhoI-ClaI derivative; Q513L allele; bla | GenScript |
| RRDR_D516V | RRDR-XhoI-ClaI derivative; D516V allele; bla | GenScript |
| RRDR_H526Y | RRDR-XhoI-ClaI derivative; H526Y allele; bla | GenScript |
| RRDR_S531L | RRDR-XhoI-ClaI derivative; S531L allele; bla | GenScript |
| RRDR_L533P | RRDR-XhoI-ClaI derivative; L533P allele; bla | GenScript |
| orfX-SCC | *Staphylococcus aureus* orfX and 480 bp SCC downstream; bla | GenScript |
| RRDR-57-HAI | RRDR-XhoI-ClaI derivative; hyg; L5-attP-int | This work |
| 513-57-HAI | RRDR_Q513L derivative; hyg; L5-attP-int | This work |
| 516-57-HAI | RRDR_D516V derivative; hyg; L5-attP-int | This work |
| 526-57-HAl | RRDR_H526Y derivative; hyg; L5-attP-int | This work |
| 531-57-HAI | RRDR_S531L derivative; hyg; L5-attP-int | This work |
| 533-57-HAI | RRDR_L533P derivative; hyg; L5-attP-int | This work |
| orfX-SCC-57-HAI | orfX-SCC derivative; hyg; L5-attP-int | This work |

TABLE 3

| Nucleic acid sequence inserts used in the study | |
|---|---|
| Sequence Element | Nucleic acid sequence |
| $RRDR_{TB-wt}$ (SEQ ID NO:9) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC<br>AACATCCGGCCGGTGGTCGCCGCGATCAAGGAGTTCTTCGGCAC<br>CAGCCAGCTGAGCCAATTCATGGACCAGAACAACCCGCTGTCGG<br>GGTTGACCCACAAGCGCCGACTGTCGGCGCTGGGGCCCGGCGG<br>TCTGTCACGTGAGCGTGCCGGGCTGGAGGTCCGCGACGTGCAC<br>CCGTCGCACTACGGCCGGATGTGCCCGATCGAAACCCCTGAGG<br>GGCCCAACATCGGTCTGATCGGCTCGCTGTCGGTGTACGCGCG<br>GGTCAACCCGTTCGGGTTCATCGAAACGCCGTACCGCAAGGTG |
| $RRDR_{TB-513}$ (SEQ ID NO: 10) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC<br>AACATCCGGCCGGTGGTCGCCGCGATCAAGGAGTTCTTCGGCAC<br>CAGCCAGCTGAGCCTATTCATGGACCAGAACAACCCGCTGTCGG<br>GGTTGACCCACAAGCGCCGACTGTCGGCGCTGGGGCCCGGCGG<br>TCTGTCACGTGAGCGTGCCGGGCTGGAGGTCCGCGACGTGCAC<br>CCGTCGCACTACGGCCGGATGTGCCCGATCGAAACCCCTGAGG<br>GGCCCAACATCGGTCTGATCGGCTCGCTGTCGGTGTACGCGCG<br>GGTCAACCCGTTCGGGTTCATCGAAACGCCGTACCGCAAGGTG |
| $RRDR_{TB-516}$ (SEQ ID NO: 11) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC |

TABLE 3-continued

Nucleic acid sequence inserts used in the study

| Sequence Element | Nucleic acid sequence |
|---|---|
| | AACATCCGGCCGGTGGTCGCCGCGATCAAGGAGTTCTTCGGCAC<br>CAGCCAGCTGAGCCAATTCATGGTCCAGAACAACCCGCTGTCGG<br>GGTTGACCCACAAGCGCCGACTGTCGGCGCTGGGGCCCGGCGG<br>TCTGTCACGTGAGCGTGCCGGGCTGGAGGTCCGCGACGTGCAC<br>CCGTCGCACTACGGCCGGATGTGCCCGATCGAAACCCCTGAGG<br>GGCCCAACATCGGTCTGATCGGCTCGCTGTCGGTGTACGCGCG<br>GGTCAACCCGTTCGGGTTCATCGAAACGCCGTACCGCAAGGTG |
| $RRDR_{TB-526}$ (SEQ ID NO: 12) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC<br>AACATCCGGCCGGTGGTCGCCGCGATCAAGGAGTTCTTCGGCAC<br>CAGCCAGCTGAGCCAATTCATGGACCAGAACAACCCGCTGTCGG<br>GGTTGACCTACAAGCGCCGACTGTCGGCGCTGGGGCCCGGCGG<br>TCTGTCACGTGAGCGTGCCGGGCTGGAGGTCCGCGACGTGCAC<br>CCGTCGCACTACGGCCGGATGTGCCCGATCGAAACCCCTGAGG<br>GGCCCAACATCGGTCTGATCGGCTCGCTGTCGGTGTACGCGCG<br>GGTCAACCCGTTCGGGTTCATCGAAACGCCGTACCGCAAGGTG |
| $RRDR_{TB-531}$ (SEQ ID NO: 13) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC<br>AACATCCGGCCGGTGGTCGCCGCGATCAAGGAGTTCTTCGGCAC<br>CAGCCAGCTGAGCCAATTCATGGACCAGAACAACCCGCTGTCGG<br>GGTTGACCCACAAGCGCCGACTGTTGGCGCTGGGGCCCGGCGG<br>TCTGTCACGTGAGCGTGCCGGGCTGGAGGTCCGCGACGTGCAC<br>CCGTCGCACTACGGCCGGATGTGCCCGATCGAAACCCCTGAGG<br>GGCCCAACATCGGTCTGATCGGCTCGCTGTCGGTGTACGCGCG<br>GGTCAACCCGTTCGGGTTCATCGAAACGCCGTACCGCAAGGTG |
| $RRDR_{TB-533}$ (SEQ ID NO: 14) | GCTGACCGAAGAAGACGTCGTGGCCACCATCGAATATCTGGTCC<br>GCTTGCACGAGGGTCAGACCACGATGACCGTTCCGGGCGGCGT<br>CGAGGTGCCGGTGGAAACCGACGACATCGACCACTTCGGCAAC<br>CGCCGCCTGCGTACGGTCGGCGAGCTGATCCAAAACCAGATCC<br>GGGTCGGCATGTCGCGGATGGAGCGGGTGGTCCGGGAGCGGA<br>TGACCACCCAGGACGTGGAGGCGATCACACCGCAGACGTTGATC<br>AACATCCGGCCGGTGGTCGCCGCGATCAAGGAGTTCTTCGGCAC<br>CAGCCAGCTGAGCCAATTCATGGACCAGAACAACCCGCTGTCGG<br>GGTTGACCCACAAGCGCCGACTGTCGGCGCCGGGGCCCGGCG<br>GTCTGTCACGTGAGCGTGCCGGGCTGGAGGTCCGCGACGTGCA<br>CCCGTCGCACTACGGCCGGATGTGCCCGATCGAAACCCCTGAG<br>GGGCCCAACATCGGTCTGATCGGCTCGCTGTCGGTGTACGCGC<br>GGGTCAACCCGTTCGGGTTCATCGAAACGCCGTACCGCAAGGTG |
| SCCmec (SEQ ID NO: 8) | ATGAAAATCACCATTTTAGCTGTAGGGAAACTAAAAGAGAAATATT<br>GGAAGCAAGCCATAGCAGAATATGAAAAACGTTTAGGCCCATACA<br>CCAAGATAGACATCATAGAAGTTACAGACGAAAAAGCACCAGAAA<br>ATATGAGCGACAAAGAAATCGAGCAAGTAAAAGAAAAAGAAGGC<br>CAACGAATACTAGCCAAAATCAAACCACAATCCACAGTCATTACA<br>TTAGAAATACAAGGAAAGATGCTATCTTCCGAAGGATTGGCCCAA<br>GAATTGAACCAACGCATGACCCAAGGGCAAAGCGACTTTGTATTC<br>GTCATTGGCGGATCAAACGGCCTGCACAAGGACGTCTTACAACG<br>TAGTAACTACGCACTATCATTCAGCAAAATGACATTTCCACATCAA<br>ATGATGCGGGTTGTGTTAATTGAACAAGTGTACAGAGCATTTAAG<br>ATTATGCGTGGAGAAGCATATCATAAATGATGCGGTTTTTTCAGC<br>CGCTTCATAAAGGGATTTTGAATGTATCAGAACATATGAGGTTTAT<br>GTGAATTGCTGTTATGTTTTTAAGAAGCTTATCATAAGTAATGAGG<br>TTCATGATTTTTGACATAGTTAGCCTCCGCAGTCTTTCATTTCAAG<br>TAAATAATAGCGAAATATTCTTTATACTGAATACTTATAGTGAAGC<br>AAAGTTCTAGCTTTGAGAAAATTCTTTCTGCAACTAAATATAGTAA<br>ATTACGGTAAAATATAAATAAGTACATATTGAAGAAAATGAGACAT<br>AATATATTTTATAATAGGAGGGAATTTCAAATGATAGACAACTTTA<br>TGCAGGTCCTTAAATTAATTAAAGAGAAACGTACCAATAATGTAGT<br>TAAAAAATCTGATTGGGATAAAGGTGATCTATATAAAACTTTAGTC<br>CATGATAAGTTACCCAAGCAGTTAAAAGTGCATATAAAAGAAGAT<br>AAATATGA |

*E. coli* strains were grown at 37° C. in standard Luria Bertani (LB) or 2YT liquid medium or on solid medium (LA) supplemented with the appropriate antibiotics at concentrations of 100-200 μg/ml ampicillin, 200 μg/ml hygromycin B (hyg) or 50 μg/ml kanamycin (kan). *Mycobacterium smegmatis* strains were grown at 37° C. shaking in Middlebrook 7H9 liquid medium (Difco) supplemented with 0.085% NaCl, 0.2% glucose, 0.2% glycerol and 0.05% Tween80, or on Middlebrook 7H10 solid medium (Difco) supplemented with 0.085% NaCl, 0.2% glucose and 0.5% glycerol. Antibiotics were used at concentrations of 50 μg/ml hygromycin, 200 μg/ml RIF or 25 μg/mL kanamycin.

Example 2

Introduction of Plasmid DNA into *Mycobacterium smegmatis* by Electroporation

Electrocompetent $mc^2155$ were prepared as follows: Cells were grown to log phase ($OD_{600}$ 0.5-0.9) and harvested by centrifugation (3 500 rpm, 10 min, 4° C.). The pelleted cells were then washed three times by gentle resuspension in 10 ml ice-cold 10% glycerol and cells pelleted by centrifugation between washes (3 500 rpm, 10 min, 4° C.). The cells were resuspended in an appropriate volume of ice-cold 10% glycerol and used immediately. For transformation, 400 μl of electro-competent cells were transferred to pre-chilled 0.2 cm electroporation cuvettes (Bio-Rad), together with plasmid DNA. The Gene PulserX cell (Bio-Rad) was used for electroporation set at 2.5 kV, 25 ρF and 10000. Cells were immediately rescued with 1 ml of 2×TY for 3 hours or overnight at 37° C. with shaking at 100 rpm. The rescued cells were plated on Middlebrook 7H10 supplemented with hyg where appropriate, and incubated for 3 days at 37° C.

Example 3

Cloning of Shuttle Plasmids for Integration into *Mycobacterium smegmatis*

Integrating shuttle vectors were cloned by combining pUC57-simple based vectors bearing the sequence of interest with the NruI/ScaI 2709 bp fragment from pHINT containing an attP-int fragment from mycobacteriophage L5 together with the resistance marker gene. The resulting vectors are capable of plasmid replication in DH5α as well as integration into the attB site of mycobacteriophage L5. The foreign nucleotide sequences were either *Mycobacterium tuberculosis*-based, spanning the RRDR region (SEQ ID NOs:1-6), or from *Staphylococcus aureus* (SEQ ID NO:8). For detection of $RIF^R$ alleles the collection of SNPs represented in the panel was based on frequently occurring clinical samples within the RRDR region, namely Q513L, D516V, H526Y, S531L, and L533P. For the MRSA assay 480 bp on either side of the SCCmec junction were included (SEQ ID NO:8).

Plasmid constructs that were amp and hyg resistant were confirmed by restriction mapping and after introduction by electroporation into *Mycobacterium smegmatis*, single colonies were selected from hyg-supplemented solid medium. Clones were stored at −80° C. in glycerol and used for analysis in standard GeneXpert® diagnostics in parallel with clinical samples, with units that had been calibrated by standard methods.

Example 4

Analysis of Strains by Standard GeneXpert Laboratory Diagnostics for Xpert®-MTB/RIF Assay.

Single colonies of wild type or modified *Mycobacterium smegmatis* strains were picked and grown in liquid 7H9 medium supplemented with hyg where appropriate. Bacteria were grown to stationary phase and 300 μl of 10-fold dilutions from $10^{-2}$ to $10^{-4}$ were added to 3 ml of the lysis buffer supplied by the manufacturer. Samples were processed at the National Health Laboratory Services of South Africa (NHLS) in parallel with clinical specimens. Xpert®-MTB/RIF was used to test for $RRDR_{TB}$ and its variants.

The digital output of the Xpert®-MTB/RIF tests was analysed and the results are shown in Table 4. From wild type *Mycobacterium smegmatis* in the Xpert®-MTB/RIF assay, fluorescent signal was obtained from Probe C only, which is located at 16 bp with 100% homology between $RRDR_{TB}$ and $RRDR_{SM}$ (FIG. 1). The strain was flagged as “MTB NOT DETECTED”. Xpert®-MTB/RIF requires signal from three or more probes for positive identification (Xpert® MTB/RIF package insert). Positive signal was obtained in strain dreem1 for all 5 probes A to E. This is consequently flagged as “MTB DETECTED” and classified as either HIGH, MEDIUM or LOW with different dilutions. For the other strains, dreem2 to dreem6, signal was obtained for four of the five probes, again flagging them as “MTB DETECTED”.

The location of the SNPs in the different strains led to probe failures as expected (Table 4). For example, lack of signal was observed for Probe B in strains dreem2 (Q513L) and dreem3 (D516V), for Probe D in dreem4 (H526Y), and for Probe E in dreem5 (S531L) and dreem6 (L533P). The customised software supplied with the cartridges for Xpert®-MTB/RIF uses a fixed program that calculates the output based on numerical data. According to this, even though signal is obtained from probes for Q513L, D516V and L533P with fewer numbers of bacteria, RIFR is correctly assigned for 14 of the 15 assays (93%). For clone dreem2 (D516V) at a dilution of 10-4 the Ct value of 27 is beyond the cut off value of 25.

TABLE 4

Results from the Xpert ® MTB/RIF assays

| | $RRDR_{TB}$ mutation | Dilution | MTB Detected | $RIF^R$ | Probe A $C_t$ | Probe A End | | Probe B Q513L D516V $C_t$ | Probe B End | | Probe C $C_t$ | Probe C End | | Probe D H526Y $C_t$ | Probe D End | | Probe E S531L L533P $C_t$ | Probe E End | |
|---|---|---|---|---|---|---|---|---|---|---|---|---|---|---|---|---|---|---|---|
| $mc^2155$ | N/A | | NOT | N/A | 0 | 5 | – | 0 | 7 | – | 29 | 38 | + | 0 | 3 | – | 0 | 3 | – |
| dreem1 | wild type | $10^{-3}$ | MED | no | 18 | 150 | + | 20 | 140 | + | 18 | 220 | + | 20 | 210 | + | 20 | 120 | + |
| | | $10^{-4}$ | LOW | no | 22 | 172 | + | 25 | 131 | + | 23 | 236 | + | 24 | 234 | + | 23 | 176 | + |
| | | $10^{-5}$ | LOW | no | 25 | 127 | + | 25 | 115 | + | 24 | 190 | + | 25 | 177 | + | 25 | 139 | + |

TABLE 4-continued

Results from the Xpert ® MTB/RIF assays

| | $RRDR_{TB}$ mutation | Dilution | MTB Detected | $RIF^R$ | Probe A $C_t$ | Probe A End | | Probe B Q513L D516V $C_t$ | Probe B Q513L D516V End | | Probe C $C_t$ | Probe C End | | Probe D H526Y $C_t$ | Probe D H526Y End | | Probe E S531L L533P $C_t$ | Probe E S531L L533P End | |
|---|---|---|---|---|---|---|---|---|---|---|---|---|---|---|---|---|---|---|---|
| dreem2 | Q513L | $10^{-2}$ | HIGH | yes | 15 | 184 | + | 0 | 7 | – | 15 | 272 | + | 16 | 253 | + | 17 | 132 | + |
| | | $10^{-3}$ | MED | yes | 21 | 235 | + | 0 | 17 | – | 22 | 272 | + | 23 | 305 | + | 23 | 180 | + |
| | | $10^{-4}$ | LOW | no | 24 | 130 | + | 27 | 71 | + | 25 | 166 | + | 26 | 163 | + | 26 | 129 | + |
| dreem3 | D516V | $10^{-2}$ | HIGH | yes | 11 | 134 | + | 0 | −12 | – | 11 | 221 | + | 13 | 215 | + | 13 | 104 | + |
| | | $10^{-3}$ | HIGH | yes | 16 | 164 | + | 0 | 10 | – | 17 | 224 | + | 18 | 224 | + | 18 | 128 | + |
| | | $10^{-4}$ | MED | yes | 21 | 144 | + | 41 | 2 | – | 21 | 200 | + | 22 | 204 | + | 22 | 128 | + |
| dreem4 | H526Y | $10^{-2}$ | HIGH | yes | 13 | 235 | + | 15 | 148 | + | 13 | 336 | + | 0 | 7 | – | 15 | 167 | + |
| | | $10^{-3}$ | MED | yes | 17 | 179 | + | 20 | 99 | + | 17 | 251 | + | 0 | 7 | – | 17 | 151 | + |
| | | $10^{-4}$ | MED | yes | 21 | 191 | + | 24 | 114 | + | 22 | 240 | + | 0 | 14 | – | 22 | 166 | + |
| dreem5 | S531L | $10^{-2}$ | HIGH | yes | 15 | 232 | + | 17 | 169 | + | 16 | 349 | + | 17 | 383 | + | 0 | −8 | – |
| | | $10^{-3}$ | MED | yes | 19 | 163 | + | 21 | 143 | + | 20 | 231 | + | 21 | 241 | + | 0 | −3 | – |
| | | $10^{-4}$ | MED | yes | 22 | 132 | + | 23 | 134 | + | 22 | 206 | + | 23 | 203 | + | 0 | −1 | – |
| dreem6 | L533P | $10^{-2}$ | HIGH | yes | 14 | 173 | + | 16 | 140 | + | 15 | 262 | + | 16 | 282 | + | 0 | −8 | – |
| | | $10^{-3}$ | MED | yes | 18 | 149 | + | 19 | 131 | + | 18 | 213 | + | 19 | 233 | + | 25 | 24 | + |
| | | $10^{-4}$ | MED | yes | 20 | 138 | + | 22 | 130 | + | 21 | 198 | + | 22 | 210 | + | 26 | 37 | + |

Example 5

Analysis of Strains by Standard GeneXpert® Laboratory Diagnostics for Xpert®-SANC Assay A single colony of wild type $mc^2155$ or modified *Mycobacterium smegmatis* strain dreemX was picked and grown in liquid 7H9 medium supplemented with hyg where appropriate. Bacteria were grown to stationary phase and 10 μl of neat culture were added to 3 ml of the lysis buffer supplied by the manufacturer. Samples were processed at the National Health Laboratory Services of South Africa (NHLS). Xpert®-SANC was used to test for the orfX-SCC junction of methicillin resistant *Staphylococcus aureus* (Table 5).

TABLE 5

Results from the Xpert ®-SANC assay

| | | spa $C_t$ | spa End | | mecA $C_t$ | mecA End | | SCCmec $C_t$ | SCCmec End | |
|---|---|---|---|---|---|---|---|---|---|---|
| $mc^2155$ | MRSA NEGATIVE; SA NEGATIVE | 0 | 0 | – | 0 | 7 | – | 0 | 3 | – |
| dreemX | MRSA NEGATIVE; SA NEGATIVE | 0 | 1 | – | 0 | 4 | – | 25 | 460 | + |
| dreemX | MRSA NEGATIVE; SA NEGATIVE | 0 | 1 | – | 0 | −2 | – | 21 | 459 | + |

Figure 3:
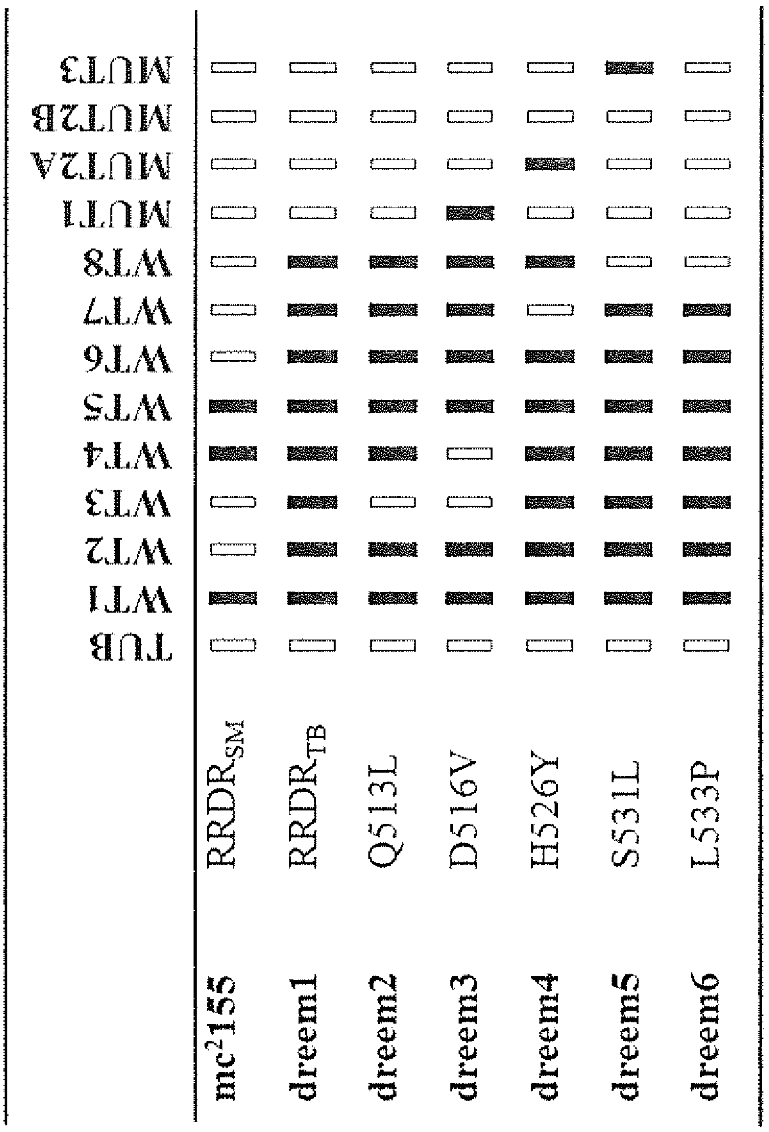
FIG. 3: Results from the Hain LPA MTBDRplus assay. No TUB hybridisation was seen in all *Mycobacterium smegmatis* strains. Resistance profiling analysis is shown only for RIF but not INH resistance. No hybridisation was obtained for either the katG or the inhA loci. Black boxes denote positive for hybridisation signal. White boxes denote absence of hybridisation signal. The single grey box in strain dreem4 denotes weak hybridisation signal.

In the Xpert®-SANC module none of the probes spa, mecA or SCCmec produced fluorescent signal from parental *Mycobacterium smegmatis* as expected (FIG. 3). Identification is based on signal from the chromosomal staphylococcal protein A (spa) gene which is specific for *Staphylococcus aureus*. In strain dreemX, in which the orfX-SCC junction was introduced at the L5-attP site, the SCCmec probe gave positive signal with a $C_t$ value of 25 and an endpoint of 460. The strain was flagged as "MRSA Negative; SA Negative".

Example 6

Analysis of Strains by Standard Hain Lifescience MDRTBplus and GenoType *Mycobacterium* CM Line Probe Assays (LPA).

Single colonies of mutant strains were picked from solid plates and suspended in 500 μl of molecular biology grade water. Samples were processed at the NHLS in parallel with clinical specimens. Results were scored visually from the hybridisation strips and recorded as presence or absence of probe signal.

Results from Hain MDRTBplus analysis flagged all *Mycobacterium smegmatis*-derived strains as *Mycobacterium tuberculosis* negative (Table 6). This is to be expected because the test probe TUB for the *Mycobacterium tuberculosis* complex (MTBC) is located at the intergenic spacer region of 16S-23S rRNA and was designed to be highly specific. When the strains were analysed using the Hain GenoType *Mycobacterium* CM VER 2.0 they were consistently identified as *Mycobacterium fortuitum/Mycobacterium mageritense*. This assay is performed as standard procedure at the NHLS in South Africa for all clinical samples which are identified as non-MTBC, to classify the causative agent in the patient.

TABLE 6

Results from the Hain LPA MTBDRplus assay. Results are only shown for RIF resistance analysis, not INH resistance. No hybridisation was obtained for either the katG or the inhA loci

| $RRDR_{TB}$ mutation | $mc^2155$ N/A | dreem1 wild type | dreem2 Q513L | dreem3 D516V | dreem4 H526Y | dreem5 S531L | dreem6 L533P |
|---|---|---|---|---|---|---|---|
| TUB | – | – | – | – | – | – | – |
| WT1 | + | + | + | + | + | + | + |
| WT2 | | + | + | + | + | + | + |
| WT3 | | + | – | – | + | + | + |
| WT4 | + | + | + | (+) | + | + | + |
| WT5 | + | + | + | + | + | + | + |
| WT6 | | + | + | + | + | + | + |
| WT7 | | + | + | + | – | + | + |
| WT8 | | + | + | + | + | | |
| MUT1 | | | | + | | | |
| MUT2A | | | | | + | | |
| MUT3 | | | | | | + | |

In the MDRTBplus assay of *Mycobacterium smegmatis*, three bands hybridise: WT1, WT4 and WT5 (Table 5). These lie at sequences of 100% homology between $RRDR_{SM}$ and $RRDR_{TB}$ (FIG. 1). All eight probes WT1-WT8 (Table 5) bound in strain dreem1, which contains $RRDR_{SM}$ and $RRDR_{TB}$. SNPs positioned at probes WT1, WT4 and WT5 cannot be assayed because lack of binding to $RRDR_{TB}$ is obscured by binding to $RRDR_{SM}$. In strains dreem2 to dreem6 hybridisation banding was as expected from strains dreem4, dreem5 and dreem6. Strains dreem2 and dreem3 were difficult to interpret where hybridising intensity of bands was intermediate. WT2 in dreem2 was expected not to hybridise, while WT4 was expected to hybridise strongly, but both of these bound weakly. In strains dreem3, dreem4 and dreem5 the presence of the mutant alleles was positively identified by hybridising bands with the respective SNPs as expected: MUT1 (D516V), MUT2A (H526Y) and MUT3 (S531L), respectively (FIG. 3). No bands were obtained for katG or inhA in the *Mycobacterium smegmatis* strains, indicating divergence at these loci between *Mycobacterium tuberculosis* and *Mycobacterium smegmatis*.

The *Mycobacterium smegmatis* strains developed and tested in this study were able to mimic the gene content of *Mycobacterium tuberculosis* and *Staphylococcus aureus* origin. The Applicant has shown that these strains could produce signal as expected, based on the NAA nature of the assays. The clinical applicability of this methodology as a positive control for diagnostic purposes has wide ranging implications. It enables calibration and validation of GeneXpert® modules leading to confidence in diagnostic results as an external standard, eliminating the necessity for in-house standards which vary across laboratories. An example of such a calibration and validation system is in place for the Xpert®-MTBIRIF assay which makes use of SmartSpot dried culture spots (DCS) as an external quality control. These are currently produced based on killed *Mycobacterium tuberculosis* strains processed in BSLIII laboratories.

The advantages of the strains generated in this study are that they can be used to produce control samples in a BSLII facility which: (i) ensures that all samples are non-biohazardous; (ii) allows for control samples of $RIF^R$ $RRDR_{TB}$ alleles from mycobacterial strains that are phenotypically $RIF^S$; (iii) requires staff trained only at BSLII level, not BSLIII level; (iv) reduces the turnaround time required to produce batches of control samples; and (iv) reduces the cost of production compared to that of BSLIII laboratories.

Use of the Xpert®-MTB/RIF and MTBDRplus diagnostic assays do have limitations regarding $RIF^R$ determination. $RRDR_{SM}$ and $RRDR_{TB}$ contain regions of 100% homology located at Probe C for Xpert®-MTBIRIF and at WT1, WT4 and WT5 for MTBDRplus. Accordingly positive signal at these loci is obtained for all *Mycobacterium smegmatis* strains tested. This precludes use of both methods for SNPs located at those positions, as lack of binding within the distal $RRDR_{TB}$ is masked by binding to $RRDR_{SM}$, and thus positive signal will be detected, either by fluorescent signal using Xpert®-MTB/RIF or positive hybridisation in MTBDRplus.

SNPs located within any of the other probes will be detectable by loss of signal as the genomic content at those loci effectively reverts to the wild type *Mycobacterium smegmatis* $RRDR_{SM}$. Inherent in the design of both assays is the fact that loss of signal cannot identify the nature of the mutation, where loss of signal is an indicator. In the case of MTBDRplus four specific SNPs have been selected based on prior knowledge of their frequencies in clinical studies, namely D516V, H526Y, H526D and S531L. For these sequences, the new bands hybridise at MUT1, MUT2A, MUT2B and MUT3, respectively. The inclusion of these variants in the LPA strips is thus a positive indicator of acquisition of mutant SNPs leading to resistance and more reliable than the negative results of band drop-out due to loss of wild type SNPs.

Because the integrated $RRDR_{TB}$ sequence in this study is present at a distal locus as a non-transcribed nucleotide sequence it does not confer $RIF^R$ to the bacteria. The mutation would need to be incorporated into the fully transcribed essential RpoB protein. Introduction of a second copy of the full length rpoB gene with SNPs V146F and 1572F that had been identified outside RRDR in clinical $RIF^R$ strains has been able to confer resistance by a dominant-positive mechanism. The integrating nature of the shuttle delivery vector used herein makes use of strains that are antibiotic resistant. In this case the selectable marker $hyg^R$ but $RIF^S$.

Although the Xpert® MTB/RIF and MDRTBplus methods are both molecular in nature, their difference lies in the readout. In the case of Xpert®, the molecular beacon technology is both specific and quantitative with respect to TB identification. The cycle threshold $C_t$ is an indication of template amount, where higher numbers of bacteria produce fluorescent signal at sooner time points due to the fact that more genomic equivalents are present. Fewer bacteria result in later appearance of signal, and a cycle threshold above 25 is considered close to or below the detection limit. Speciation depends on the combined fluorescent signals obtained from the different probes at the RRDR locus itself. Mathematical computer programmes are supplied for each GeneXpert® module that cannot be altered by the user. The digital output determines the identity of the RRDR, its quantity and the location of possible SNPs (Xpert® MTB/RIF package insert). In the case of MDRTBplus, the readout is taken as the final product of multiplex PCR. This includes four loci and thus four sets of primers: for speciation (rrnA), RIF resistance ($RRDR_{TB}$) and INH resistance (katG and inhA). The result upon hybridisation is either the loss or gain of specific bands, which is not numerically indicative of bacterial load. It also allows for specific characterisation of mutated alleles that have been included separately as additional probes.

This problem could be circumvented by replacement of $RRDR_{SM}$ with $RRDR_{TB}$ at the native locus. However, this approach would result in strains that are phenotypically RIFA because the RpoB peptide sequence would be altered and affect RNAP binding.

The Xpert®-SANC assay was tested on *Mycobacterium smegmatis*-derived strain dreemX and was able to produce specific signal generated from probe SCCmec, which is present in many MRSA strains containing SCC integrating modules. Not all of these necessarily carry a mecA gene, and so the SCCmec probe was chosen for this study. The result indicates that the Xpert®-SANC module is able to successfully lyse the mycobacteria in the supplied cartridge using the sonic lysis procedure. *Staphylococcus aureus* is Gram positive and its cell wall consists only of the cell membrane and a thick peptidoglycan wall. Mycobacteria in addition have particularly thick, impenetrable and lipid-rich cell walls, yet this does not prevent release of DNA as template for the cycling procedure. The high G+C content (ca. 67%) of mycobacterial DNA was of concern because of possible interference with the cycling and binding parameters optimised for *Staphylococcus aureus* which has a G+C content of ca. 33%. This was not observed with the SCCmec probe tested herein. For the results obtained, the fluorescence curve obtained did not have significant background signal (data not shown) which could mean that the PCR product and/or probe binding is sufficiently specific, or possibly because of the A+T bias of the *Staphylococcus aureus* nucleotide sequence compared to the G+C bias of the *Mycobacterium smegmatis* chromosome.

The invention claimed is:

1. A diagnostic control composition comprising a recombinant bacterium, wherein the recombinant bacterium is a non-pathogenic *Mycobacterium smegmatis* bacterium having a modified genome containing a staphylococcal cassette chromosome mec (SCCmec) junction region of *Staphylococcus aureus* having a nucleic acid sequence at least 90% identical to SEQ ID NO: 8, wherein the SCCmec junction region is detectable by a molecular diagnostic assay for detecting the SCCmec junction region and wherein the recombinant bacterium mimics the diagnostic profile of *Staphylococcus aureus*.

2. The diagnostic control composition of claim 1, wherein the recombinant bacterium mimics the diagnostic profile of a methicillin resistant *Staphylococcus aureus* strain in the molecular diagnostic assay.

3. The diagnostic control composition of claim 1, wherein the recombinant bacterium further comprises a selection marker.

4. The diagnostic control composition of claim 1, wherein the recombinant bacterium is either stably or transiently transformed with a vector comprising the SCCmec junction region of *Staphylococcus aureus*.

5. A method of producing a recombinant bacterium that mimics the diagnostic profile of *Staphylococcus aureus* in a molecular diagnostic assay, the method comprising:

(i) transforming a non-pathogenic *Mycobacterium smegmatis* with a vector, wherein the vector comprises a staphylococcal cassette chromosome mec (SCCmec) junction region of *Staphylococcus aureus* having a nucleic acid sequence at least 90% identical to SEQ ID NO: 8 and a selection marker, and further wherein the SCCmec junction region is capable of being detected by the molecular diagnostic assay; and (ii) culturing the recombinant bacterium obtained in step (i) under selective conditions in order to select the recombinant bacterium.

6. The method of claim 5, wherein the recombinant bacterium mimics the diagnostic profile of a methicillin resistant *Staphylococcus aureus* strain in the molecular diagnostic assay.

7. A kit comprising the diagnostic control composition of claim 1 and instructions for use in a molecular diagnostic assay for detecting a *Staphylococcus aureus* strain.

8. The kit of claim 7, wherein the molecular assay is for detecting a methicillin resistant *Staphylococcus aureus* strain.

* * * * *

SEQUENCE LISTING

```
<160> NUMBER OF SEQ ID NOS: 14

<210> SEQ ID NO 1
<211> LENGTH: 80
<212> TYPE: DNA
<213> ORGANISM: Mycobacterium tuberculosis

<400> SEQUENCE: 1

gcaccagcca gctgagccaa ttcatggacc agaacaaccc gctgtcgggg ttgacccaca      60

agcgccgact gtcggcgctg                                                  80


<210> SEQ ID NO 2
<211> LENGTH: 80
<212> TYPE: DNA
<213> ORGANISM: Mycobacterium tuberculosis

<400> SEQUENCE: 2

gcaccagcca gctgagccta ttcatggacc agaacaaccc gctgtcgggg ttgacccaca      60

agcgccgact gtcggcgctg                                                  80


<210> SEQ ID NO 3
<211> LENGTH: 80
<212> TYPE: DNA
<213> ORGANISM: Mycobacterium tuberculosis

<400> SEQUENCE: 3

gcaccagcca gctgagccaa ttcatggtcc agaacaaccc gctgtcgggg ttgacccaca      60

agcgccgact gtcggcgctg                                                  80


<210> SEQ ID NO 4
<211> LENGTH: 80
<212> TYPE: DNA
<213> ORGANISM: Mycobacterium tuberculosis

<400> SEQUENCE: 4

gcaccagcca gctgagccaa ttcatggacc agaacaaccc gctgtcgggg ttgacctaca      60

agcgccgact gtcggcgctg                                                  80
```

<210> SEQ ID NO 5
<211> LENGTH: 80
<212> TYPE: DNA
<213> ORGANISM: Mycobacterium tuberculosis

<400> SEQUENCE: 5
gcaccagcca gctgagccaa ttcatggacc agaacaaccc gctgtcgggg ttgacccaca 60
agcgccgact gttggcgctg 80

<210> SEQ ID NO 6
<211> LENGTH: 80
<212> TYPE: DNA
<213> ORGANISM: Mycobacterium tuberculosis

<400> SEQUENCE: 6
gcaccagcca gctgagccaa ttcatggacc agaacaaccc gctgtcgggg ttgacccaca 60
agcgccgact gtcggcgccg 80

<210> SEQ ID NO 7
<211> LENGTH: 80
<212> TYPE: DNA
<213> ORGANISM: Mycobacterium smegmatis

<400> SEQUENCE: 7
gcaccagcca gctgtcgcag ttcatggacc agaacaaccc gctgtcgggt ctgacccaca 60
agcgtcgtct ttcggcgctg 80

<210> SEQ ID NO 8
<211> LENGTH: 962
<212> TYPE: DNA
<213> ORGANISM: artificial sequence
<220> FEATURE:
<223> OTHER INFORMATION: S. aureus-derived orfX and SCCmec included in M. smegmatis

<400> SEQUENCE: 8
atgaaaatca ccattttagc tgtagggaaa ctaaaagaga aatattggaa gcaagccata 60
gcagaatatg aaaaacgttt aggcccatac accaagatag acatcataga agttacagac 120
gaaaaagcac cagaaaatat gagcgacaaa gaaatcgagc aagtaaaaga aaaagaaggc 180
caacgaatac tagccaaaat caaaccacaa tccacagtca ttacattaga aatacaagga 240
aagatgctat cttccgaagg attggcccaa gaattgaacc aacgcatgac ccaagggcaa 300
agcgactttg tattcgtcat tggcggatca aacggcctgc acaaggacgt cttacaacgt 360
agtaactacg cactatcatt cagcaaaatg acatttccac atcaaatgat gcgggttgtg 420
ttaattgaac aagtgtacag agcatttaag attatgcgtg gagaagcata tcataaatga 480
tgcggttttt tcagccgctt cataaaggga ttttgaatgt atcagaacat atgaggttta 540
tgtgaattgc tgttatgttt ttaagaagct tatcataagt aatgaggttc atgatttttg 600
acatagttag cctccgcagt ctttcatttc aagtaaataa tagcgaaata ttctttatac 660
tgaatactta tagtgaagca aagttctagc tttgagaaaa ttctttctgc aactaaatat 720
agtaaattac ggtaaaatat aaataagtac atattgaaga aaatgagaca taatatattt 780
tataatagga gggaatttca aatgatagac aactttatgc aggtccttaa attaattaaa 840
gagaaacgta ccaataatgt agttaaaaaa tctgattggg ataaaggtga tctatataaa 900
actttagtcc atgataagtt acccaagcag ttaaaagtgc atataaaaga agataaatat 960

-continued ga 962

<210> SEQ ID NO 9
<211> LENGTH: 562
<212> TYPE: DNA
<213> ORGANISM: Mycobacterium tuberculosis

<400> SEQUENCE: 9
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240
cacaccgcag acgttgatca acatccggcc ggtggtcgcc gcgatcaagg agttcttcgg 300
caccagccag ctgagccaat tcatggacca gaacaacccg ctgtcggggt tgacccacaa 360
gcgccgactg tcggcgctgg ggcccggcgg tctgtcacgt gagcgtgccg ggctggaggt 420
ccgcgacgtg cacccgtcgc actacggccg gatgtgcccg atcgaaaccc ctgaggggcc 480
caacatcggt ctgatcggct cgctgtcggt gtacgcgcgg gtcaacccgt tcgggttcat 540
cgaaacgccg taccgcaagg tg 562

<210> SEQ ID NO 10
<211> LENGTH: 562
<212> TYPE: DNA
<213> ORGANISM: Mycobacterium tuberculosis

<400> SEQUENCE: 10
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240
cacaccgcag acgttgatca acatccggcc ggtggtcgcc gcgatcaagg agttcttcgg 300
caccagccag ctgagcctat tcatggacca gaacaacccg ctgtcggggt tgacccacaa 360
gcgccgactg tcggcgctgg ggcccggcgg tctgtcacgt gagcgtgccg ggctggaggt 420
ccgcgacgtg cacccgtcgc actacggccg gatgtgcccg atcgaaaccc ctgaggggcc 480
caacatcggt ctgatcggct cgctgtcggt gtacgcgcgg gtcaacccgt tcgggttcat 540
cgaaacgccg taccgcaagg tg 562

<210> SEQ ID NO 11
<211> LENGTH: 562
<212> TYPE: DNA
<213> ORGANISM: Mycobacterium tuberculosis

<400> SEQUENCE: 11
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240
cacaccgcag acgttgatca acatccggcc ggtggtcgcc gcgatcaagg agttcttcgg 300
caccagccag ctgagccaat tcatggtcca gaacaacccg ctgtcggggt tgacccacaa 360
gcgccgactg tcggcgctgg ggcccggcgg tctgtcacgt gagcgtgccg ggctggaggt 420
ccgcgacgtg cacccgtcgc actacggccg gatgtgcccg atcgaaaccc ctgaggggcc 480
caacatcggt ctgatcggct cgctgtcggt gtacgcgcgg gtcaacccgt tcgggttcat 540
cgaaacgccg taccgcaagg tg 562

<210> SEQ ID NO 12
<211> LENGTH: 562
<212> TYPE: DNA
<213> ORGANISM: Mycobacterium tuberculosis

<400> SEQUENCE: 12
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240
cacaccgcag acgttgatca acatccggcc ggtggtcgcc gcgatcaagg agttcttcgg 300
caccagccag ctgagccaat tcatggacca gaacaacccg ctgtcggggt tgacctacaa 360
gcgccgactg tcggcgctgg ggcccggcgg tctgtcacgt gagcgtgccg ggctggaggt 420
ccgcgacgtg cacccgtcgc actacggccg gatgtgcccg atcgaaaccc ctgaggggcc 480
caacatcggt ctgatcggct cgctgtcggt gtacgcgcgg gtcaacccgt tcgggttcat 540
cgaaacgccg taccgcaagg tg 562

<210> SEQ ID NO 13
<211> LENGTH: 562
<212> TYPE: DNA
<213> ORGANISM: Mycobacterium tuberculosis

<400> SEQUENCE: 13
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240
cacaccgcag acgttgatca acatccggcc ggtggtcgcc gcgatcaagg agttcttcgg 300
caccagccag ctgagccaat tcatggacca gaacaacccg ctgtcggggt tgacccacaa 360
gcgccgactg ttggcgctgg ggcccggcgg tctgtcacgt gagcgtgccg ggctggaggt 420
ccgcgacgtg cacccgtcgc actacggccg gatgtgcccg atcgaaaccc ctgaggggcc 480
caacatcggt ctgatcggct cgctgtcggt gtacgcgcgg gtcaacccgt tcgggttcat 540
cgaaacgccg taccgcaagg tg 562

<210> SEQ ID NO 14
<211> LENGTH: 562
<212> TYPE: DNA
<213> ORGANISM: Mycobacterium tuberculosis

<400> SEQUENCE: 14
gctgaccgaa gaagacgtcg tggccaccat cgaatatctg gtccgcttgc acgagggtca 60
gaccacgatg accgttccgg gcggcgtcga ggtgccggtg gaaaccgacg acatcgacca 120
cttcggcaac cgccgcctgc gtacggtcgg cgagctgatc caaaaccaga tccgggtcgg 180
catgtcgcgg atggagcggg tggtccggga gcggatgacc acccaggacg tggaggcgat 240

-continued

```
cacaccgcag acgttgatca acatccggcc ggtggtcgcc gcgatcaagg agttcttcgg    300

caccagccag ctgagccaat tcatggacca gaacaacccg ctgtcggggt tgacccacaa    360

gcgccgactg tcggcgccgg ggcccggcgg tctgtcacgt gagcgtgccg ggctggaggt    420

ccgcgacgtg cacccgtcgc actacggccg gatgtgcccg atcgaaaccc ctgaggggcc    480

caacatcggt ctgatcggct cgctgtcggt gtacgcgcgg gtcaacccgt tcgggttcat    540

cgaaacgccg taccgcaagg tg                                             562
```